(12) United States Patent
Wilhelmsson et al.

(10) Patent No.: US 9,012,043 B2
(45) Date of Patent: Apr. 21, 2015

(54) DESIGNED SURFACES FOR USE IN MEDICAL IMPLANTS OR INSTRUMENTS

(75) Inventors: Ola Wilhelmsson, Kungsgården (SE); Tom Eriksson, Sandviken (SE); Per Mårtensson, Nacka (SE)

(73) Assignee: Sandvik Intellectual Property AB, Sandviken (SE)

( * ) Notice: Subject to any disclaimer, the term of this patent is extended or adjusted under 35 U.S.C. 154(b) by 953 days.

(21) Appl. No.: 13/142,794

(22) PCT Filed: Dec. 21, 2009

(86) PCT No.: PCT/SE2009/051482
§ 371 (c)(1), (2), (4) Date: Sep. 19, 2011

(87) PCT Pub. No.: WO2010/077204
PCT Pub. Date: Jul. 8, 2010

(65) Prior Publication Data
US 2012/0035739 A1 Feb. 9, 2012

(30) Foreign Application Priority Data
Dec. 30, 2008 (EP) .................................. 08173116

(51) Int. Cl.
*B32B 15/04* (2006.01)
*B05D 3/00* (2006.01)
(Continued)

(52) U.S. Cl.
CPC .............. *A61L 27/50* (2013.01); *A61F 2/30767* (2013.01); *A61L 27/045* (2013.01); *A61L 27/047* (2013.01); *A61L 27/30* (2013.01); *A61L 27/306* (2013.01); *A61F 2/3094* (2013.01); *A61F 2002/30016* (2013.01); *A61F 2002/30929* (2013.01); *A61F 2002/30934* (2013.01); *A61F 2250/0019* (2013.01); *A61F 2310/00017* (2013.01);
(Continued)

(58) Field of Classification Search
USPC ......... 428/688, 689, 697, 698, 699, 701, 702, 428/704; 427/402, 404, 405, 419.1, 419.2; 623/23.53, 23.56
See application file for complete search history.

(56) References Cited

U.S. PATENT DOCUMENTS 5,308,412 A 5/1994 Shetty et al.
5,370,694 A 12/1994 Davidson
(Continued)

FOREIGN PATENT DOCUMENTS

EP 0 295 397 12/1988
EP 0 640 353 3/1995
(Continued)

*Primary Examiner* — David Sample
*Assistant Examiner* — Lauren Colgan
(74) *Attorney, Agent, or Firm* — Morgan, Lewis & Bockius LLP

(57) ABSTRACT

A medical implant device or component thereof comprising a metal substrate and a coating layer structure provided on the substrate. The coating layer structure comprises an outermost layer of a ceramic material. A bonding structure is deposited between the metal substrate and the coating layer structure. The bonding structure comprises a chromium rich layer, which is deposited onto the metal substrate surface and has a higher concentration of chromium than the metal substrate, as well as a gradient layer having a composition gradient from the chromium rich layer towards the surface of the device providing increasing proportions of a gradient material which has structural correspondence with the layer of the coating layer structure that is most adjacent to the bonding structure.

24 Claims, 4 Drawing Sheets

(51) Int. Cl.
*A61F 2/02* (2006.01)
*A61L 27/50* (2006.01)
*A61F 2/30* (2006.01)
*A61L 27/04* (2006.01)
*A61L 27/30* (2006.01)

(52) U.S. Cl.
CPC .............. *A61F2310/00029* (2013.01); *A61F 2310/00401* (2013.01); *A61F 2310/00413* (2013.01); *A61F 2310/00604* (2013.01); *A61F 2310/00634* (2013.01); *A61F 2310/00754* (2013.01); *A61F 2310/0088* (2013.01); *A61F 2310/00886* (2013.01); *A61F 2310/00892* (2013.01)

(56) References Cited

U.S. PATENT DOCUMENTS

| | | | |
|---|---|---|---|
| 5,868,796 | A | 2/1999 | Buechel et al. |
| 6,451,130 | B1 | 9/2002 | Chung et al. |
| 6,514,289 | B1 * | 2/2003 | Pope et al. ............... 623/23.6 |
| 7,048,767 | B2 | 5/2006 | Namavar |
| 7,070,623 | B2 | 7/2006 | Hunter et al. |
| 7,393,589 | B2 * | 7/2008 | Aharonov et al. ............ 428/469 |
| 7,396,501 | B2 * | 7/2008 | Pope et al. ................. 264/642 |
| 2003/0229399 | A1 | 12/2003 | Namavar |
| 2005/0191408 | A1 * | 9/2005 | Aharonov et al. ........... 427/2.27 |
| 2005/0267242 | A1 | 12/2005 | Custodero et al. |
| 2006/0271191 | A1 * | 11/2006 | Hermansson ............. 623/11.11 |
| 2007/0078521 | A1 * | 4/2007 | Overholser et al. ........ 623/23.53 |
| 2007/0158446 | A1 | 7/2007 | Wang et al. |

FOREIGN PATENT DOCUMENTS

| | | |
|---|---|---|
| EP | 1 916 007 | 4/2008 |
| EP | 1 923 079 | 5/2008 |
| WO | WO 03/003950 | 1/2003 |
| WO | WO 2004/002543 | 1/2004 |
| WO | WO 2004/058107 | 7/2004 |
| WO | WO 2004/071471 | 8/2004 |
| WO | WO 2006/007861 | 1/2006 |
| WO | 2007/004913 | 1/2007 |

* cited by examiner

DESIGNED SURFACES FOR USE IN MEDICAL IMPLANTS OR INSTRUMENTS

CROSS REFERENCE TO RELATED APPLICATIONS:

This application is a §371 National Stage Application of PCT International Application No. PCT/SE2009/051482, filed Dec. 21, 2009, and claims priority under 35 U.S.C. §119 and/or §365 to European Application No. 08173116.8 filed Dec. 30, 2008.

FIELD OF THE INVENTION

The present invention relates generally to medical implants, medical implant components or medical instruments and more specifically to such medical devices with designed surfaces. In particular, the invention relates to medical devices where the surface is designed with functional layers to meet specific demands on material properties such as resilience to deformation combined with surface hardness and surface wear resistance as well as to achieve efficient adhesion between the respective layers and the substrate.

BACKGROUND OF THE INVENTION

Medical implants and instruments that are to be used in the human body and be in direct contact with the human tissues need to fulfill several requirements. This is particularly important for implants that are intended for long term or even permanent use. An obvious requirement is that the medical device should be biocompatible, i.e. not release toxic, allergy causing or otherwise noxious substances and should not induce inflammation or rejection from the organism.

An implant also has to fulfill a number of mechanical and chemical requirements. For example, an artificial joint has articulating parts that are exposed to surface-to-surface movement with a large number of load variation cycles. This could lead to abrasion wear, where the joint is slowly worn down and where particles of the implant material is released to the surrounding tissue or even the blood stream, where it may be toxic or may cause inflammation or other complications. The implant therefore has to have great fatigue resistance against that type of abrasion wear. It may also be subjected to large mechanical forces and therefore must be strong enough to tolerate heavy and changing work loads. Since the implant will be placed in an environment of liquids and electrolytes it also needs to be resistant to corrosion.

Additionally, due to an increasing number of young and active implant recipients, and to the longer life expectancy in the population in general, there is an increasing need for high performance medical implants that are longer-lasting. Such implants should be able to withstand many years of wear and other stresses related to being positioned within the body.

Similar requirements also apply to medical instruments. These also have to be biocompatible and are often exposed to large mechanical forces as well as wear processes e.g. during surgical procedures, sterilization etc.

Metals and metal alloys are often used as the structural material for medical implants and devices. For example, titanium, zirconium and cobalt and their alloys, as well as stainless steel, are readily formed and machined into the desired shape. These metals and alloys exhibit a wide range of strengths, hardness and resistances to wear and have been found to comply rather well with many of the described requirements for a body implant. However, when used for longer periods of time or when used in implants with bearing surfaces, e.g. joint implants, where the abrasive wear processes are particularly intense, particles or debris have been found to be shed from these implants. As such debris is disposed to the surrounding tissue it may be encapsulated, induce inflammatory reactions and degradation of the tissue, eventually leading to pain and loosening of the implant. Additionally, the debris may become trapped between the bearing surfaces, thereby further increasing the rate of the wear process.

For example, one material often used in implants is an alloy of cobalt, chrome and molybdenum (CoCrMo). The alloy has been used for implants because of its strength, resistance to wear and corrosion and its biocompatibility. Under conditions of sliding wear or articulation against other bearing surfaces the alloy may, however, start to produce wear debris. It has also appeared that the cobalt content may start to dissolve and diffuse into the bloodstream, which may result in poisoning and injuries of organs. Hypersensitivity to this metal ion debris may also lead to aseptic lymphocytic vasculitis associated lesions (ALVAL), with symptoms of pain and early loosening of the implant. The risk of metal ion shedding is particularly associated with implant devices having metal-to-metal contact surfaces and appears to be lower for implants with metal-to-polymer contact surfaces.

Another material often used for implants and medical instruments is stainless steel, iron (Fe) alloyed with nickel (Ni), chrome (Cr) or Molybdenum (Mo). The material has economical advantages, but it does not have the required corrosion properties, and substances such as nickel may cause allergy.

Harder and stronger materials, such as ceramics, have also been used as the structural material for medical implants. Because of their hardness ceramic materials are more wear resistant and can withstand heavy work loads. Additionally they do not corrode. They are, however, stiffer and more brittle and have therefore, when used as structural bulk material in implants, been more prone to detrimental breaks and fractures.

In the known art a solution to these difficulties has been to use the mentioned metals and metal alloys as a base or substrate material for the main part of the implant, and modify its surface. The metals or metal alloys are ductile and have a high tensile strength, with certain tolerance to plastic deformation, and are therefore suitable as substrate materials. The surface on the other hand is designed to have better tribological properties, such as a higher hardness and strength, to better comply with the requirements on fatigue resistance and wear resistance.

One approach to design a more wear resistant surface has been to modify the surface through processes such as ion implantation, gas nitriding and high temperature oxidation. These processes mainly results in a surface modification of the substrate itself. These approaches have, however, been associated with some limitations, such as creating surfaces that are not hard enough, being too expensive or not possible to use with all kinds of desirable substrates.

Another approach, when designing a material for medical implants, has been to apply ceramic coatings to the surface of a metal or metal alloy surface, either to the whole implant or restricted to the surface areas that are most exposed to abrasive wear. Being hard and strong ceramic coatings, such as aluminum oxide ($Al_2O_3$) or zirconium oxide ($ZrO_2$), can provide a fatigue resistant surface to a metal which is resilient but sensitive to abrasion. However, due to the differences in hardness between the substrate and the surface coating and the brittleness of the ceramic, the ceramic has been found to easily crack in this conformation. As a result the coating on these types of materials are inclined to peel off, leaving shed debris and exposing the tissues to the substances of the substrate, and also leading to a dramatic increase the rate of the wear process. The tendency to peel depends both on the mechanical properties of the substrate and the coating, and on how the surface coating is adhered to the underlying substrate.

In order to avoid the tendency of the ceramic coating to crack and peel a solution has been to provide an intermediate layer between the substrate and the ceramic surface coating. The intermediate layer is designed to give a functional, mechanical and/or structural gradient throughout the layer structure, thereby providing good adhesion between the respective layers as well as a more rigid structure. For example, a layer structure having an outer layer comprising aluminum oxide ($Al_2O_3$) and an intermediate layer comprising titanium nitride (TiN), titanium carbonitride (TiCN) or titanium oxycarbonitride (TiCNO) has been provided on the surface of substrates comprising, e.g. cobalt chromium (CoCr) based alloys. It has, however, appeared that even this type of layer structure may start to wear down and peel after prolonged use in, e.g. artificial joints or other types of medical implants. There is therefore still a need for medical implants having improved durability relating to, e.g. resistance to abrasive wear.

PRIOR ART

Patent document US20070078521 A1 describes a medical implant device comprising a metal substrate, an intermediate coating other than aluminum oxide, and an outer coating of aluminum oxide, as well as a method for providing such a medical implant device. The material of the intermediate coating preferably has one or more physical or chemical properties intermediate between the physical or chemical properties of the metal substrate and the outer coating of aluminum oxide, so as to provide a transition gradient of those properties on the surface of the medical implant device. Through this transition gradient the intermediate coating can provide a desired level of adhesion between the substrate and the coating. The metal substrate can be any suitable metal other than steel; examples include cobalt, cobalt alloys, titanium and titanium alloys. The intermediate coating is adhered to the metal substrate and can comprise, e.g. titanium carbonitride (TiCN), titanium nitride (TiN), chromium nitride (CrN) or combinations thereof.

Patent document US20050191408 A1 discloses a medical implant comprising a dual layer structure deposited atop a medical grade substrate. The dual layer comprises a first ceramic layer vapor deposited atop the substrate and a second ceramic layer vapor deposited atop the first ceramic layer, such that a diffusion-bonded graded interface is produced between the respective layers. The substrate may comprise a cobalt chromium (CoCr) based medical grade alloy. The first ceramic layer is designed to adhere tightly to the substrate and may comprise titanium carbonitride. The second ceramic layer is designed to exhibit high hardness and good wear characteristics and may comprise aluminum oxide. The layers are produced by a controlled chemical vapor deposition method.

Other medical implants with ceramic coatings are also disclosed in the following patent documents US20070158446 A1, EP0295397 A1 and WO2007004913 A1.

OBJECT OF THE INVENTION

The overall object of the present invention is to provide a solution to the problem of providing a medical implant or medical instrument which is ductile and tolerant to plastic deformation, and which also exhibits good tribological properties such as high strength and resistance to abrasive wear.

It is a more specific object of the present invention to provide a solution to the problem of providing a medical implant or medical instrument with a ceramic coating which is tightly adhered to an underlying metal or metal alloy based substrate and which has a high resistance to abrasive wear and wear corrosion.

SUMMARY OF THE INVENTION

The object is solved by an improvement in a medical implant, an implant component or a medical instrument that is based on a metal substrate covered with a coating layer structure. When seeking to solve the problem of coating surfaces that are cracking and peeling after prolonged use, due to the differences in hardness between the respective layers as well as the adherence between the respective layers, the inventors have found that by adding a bonding structure between the substrate and the coating layer structure a layer structure is formed with a controllably designed gradient in hardness and structural properties. The designed layer structure thereby has better adherence between the substrate and the coating layer structure, showing improved resistance to wear and lesser risk of cracking and peeling.

The present invention provides a medical implant device or component thereof comprising a metal substrate with a coating layer structure, having at least an outermost layer of a ceramic material, provided on the substrate surface. A bonding structure is deposited between the metal substrate and the coating layer structure. The bonding structure comprises a chromium rich layer deposited onto the metal substrate surface, having a higher concentration of chromium than the metal substrate. The bonding structure also comprises a gradient layer having a composition gradient from the chromium rich layer towards the surface of the device wich provides increasing proportions of a gradient material which has structural correspondence with the layer of the coating layer structure that is most adjacent to the bonding structure. The gradient material of the bonding structure may further have structural correspondence with the chromium rich layer.

The metal substrate of the present invention comprises a metal or metal alloy, preferably with chemical and mechanical properties that are suitable for medical implants or instruments. For example, it should be ductile, and/or corrosion resistant, biocompatible (i.e. is not toxic or allergenic) and have the appropriate strength and fatigue characteristics. In one embodiment it comprises a cobalt based alloy, e.g. a cobalt chromium based alloy, or stainless steel. In a preferred embodiment the metal substrate comprises an alloy comprising carbon, such that part of the chromium rich layer may form chromium carbide (CrC), through diffusion of the carbon into the chromium layer.

The bonding structure provides a smooth transition of mechanical and/or structural properties between the metal substrate and the coating layer structure. The hardness of the bonding structure lies between the hardness of the metal substrate and the coating layer structure and increases going from the region closest to the metal substrate towards the region closest to the coating layer structure. It is also devised such that it has a structural correspondence with the metal substrate and/or the most adjacent layer of the coating layer structure. The bonding structure thereby provides a structural matching between the layers which increases adhesion between the layers.

The chromium rich layer of the bonding structure may comprise chromium carbide (CrC), chromium carbonitride (CrCN) and/or chromium nitride (CrN), and preferably comprises a first chromium compound layer of chromium carbide (CrC) and a second chromium compound layer of chromium carbonitride (CrCN). The gradient material of the bonding structure preferably comprises a selection of intermetallic carbides, intermetallic nitrides or intermetallic carbonitrides, such as titanium carbonitride (TiCN) or zirconium carbonitride (ZrCN). The total thickness of the bonding structure, including the chromium rich layer and the gradient layer, is in the range of 1-5 μm.

The outermost layer of the present invention provides a surface which is strong and wear resistant and in addition preferably is biocompatible, chemically inert and corrosion resistant. The outermost layer comprises a ceramic material preferably selected from the group of aluminum oxide ($Al_2O_3$), zirconium oxide ($ZrO_2$), titanium carbonitride (TiCN), zirconium carbonitride (ZrCN) or titanium boronitride (TiBN), or a combination thereof, and most preferably α- or κ-phase aluminum oxide ($Al_2O_3$). The outermost layer may range from about 0.5 to 10 μm.

The medical implant device may further comprise a coating layer structure having one or more intermediate layers between the bonding structure and the outermost layer. In a preferred embodiment an intermediate layer is in direct contact with the bonding structure. The purpose of the intermediate layer is to further provide a smooth transition and good adherence between the metal substrate and the outermost layer. It preferably comprises a material which has one or more mechanical, chemical or physical properties that are intermediate between the corresponding properties of the bonding structure and the outermost layer. It will thereby, in addition to the bonding structure, further provide a transition gradient of those properties, and thereby also provide an increased level of adhesion between the metal substrate and the outermost layer. The intermediate layer which is in direct contact with the bonding structure preferably comprises a material selected from the group comprising of intermetallic nitrides or intermetallic carbonitrides, such as titanium carbonitride (TiCN) or zirconium carbonitride (ZrCN) or combinations thereof and its thickness may range from 0.1 to 10 μm and is preferably in the order of 5 μm.

In a herein applied example of the present invention the medical implant device or component thereof comprises a metal substrate comprising cobalt based alloy or stainless steel and has a carbon content. A coating layer structure is provided on the substrate and a bonding structure is deposited between the metal substrate and the coating layer structure. The coating layer structure comprises an intermediate layer with titanium carbonitride (TiCN), and an outermost layer comprising aluminum oxide ($Al_2O_3$). The bonding structure comprises a chromium rich layer, having a higher concentration of chromium than the metal substrate, which is deposited onto the metal substrate surface. The bonding structure also comprises a composition gradient from the chromium rich layer towards the surface of the device providing increasing proportions of titanium carbonitride (TiCN). In addition the chromium rich layer may comprise a first chromium compound layer of chromium carbide (CrC) and a second chromium compound layer of chromium carbonitride (CrCN).

The present invention also provides a method of providing a medical implant device or component thereof A medical implant device or component thereof comprising a metal substrate is provided, upon at least a portion of which is deposited chromium in a temperature in the range of 800° C.-1100° C. A chromium rich layer is thereby created on the metal substrate surface. A gradient layer of a material composition is deposited onto the chromium rich layer such that increasing proportions of a gradient material appear outwardly from the chromium rich layer. A material forming a first layer, adjacent to the gradient layer, of a coating layer structure is deposited onto the gradient layer, where the first layer of the coatings structure has structural correspondence with the gradient material. The gradient layer may also be deposited such that the surface of the chromium rich layer forms a material having a structural correspondence with the gradient material.

The method further comprises steps to provide the properties of the medical implant device as described above.

BRIEF DESCRIPTION OF THE DRAWINGS

The invention will be explained in more detail in the following description, referring to the enclosed figures, where.

DETAILED DESCRIPTION

Overview of Designed Layer Structure

The invention provides an improvement to medical implants, medical implant components or medical instruments comprising a metal substrate covered with a coating layer structure. Such a medical device may, e.g. be based on a metal substrate with a cobalt chromium (CoCr) based alloy which is provided with a coating layer structure. The coating layer structure may comprise a single ceramic outermost layer of e.g. titanium boronitride (TiBN), oxides such as aluminum oxide ($Al_2O_3$) and zirconium oxide ($ZrO_2$) or carbonitrides of titanium (TiCN) and/or zirconium (ZrCN). The coating layer structure may alternatively comprise a multi-layered structure, e.g. with one or more intermediate layers comprising e.g. titanium carbonitride (TiCN) and a ceramic outermost layer such as aluminum oxide ($Al_2O_3$). In order to prevent these kinds of coating layer structures from cracking and peeling even after prolonged use, a bonding structure is added between the substrate and the coating layer structure. In accordance with the invention, a designed layer structure is thereby formed where an improved gradient in hardness and structural properties is provided. This has the effect that better adherence between the substrate and the coating layer structure is achieved, and as a consequence the medical implant or instrument is provided with improved resistance to wear and lesser risk of cracking and peeling.

In this context it is meant to be understood that a chemical nomenclature such as TiCN is equal to TixCyNz, i.e. it represents a material which can have different stoichiometric relationships with regard to its constituent atoms.

Figure 1A:
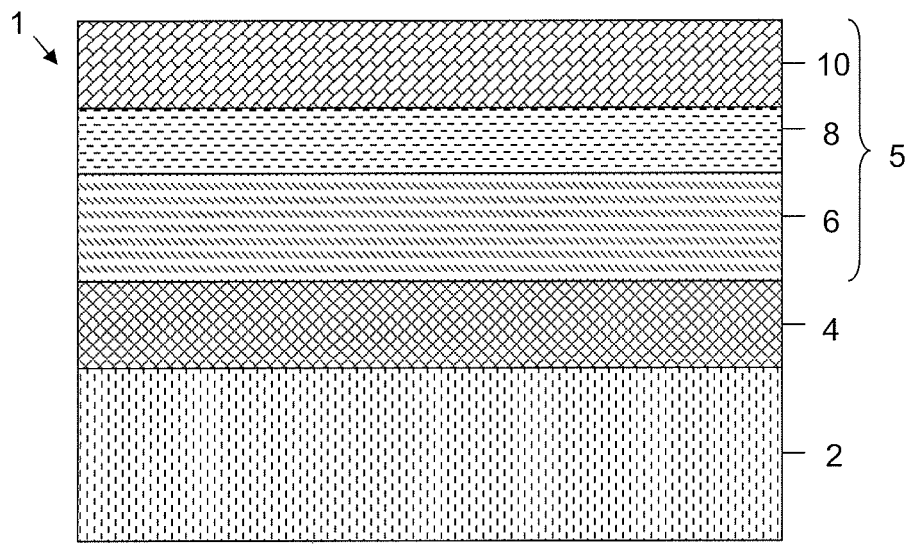
FIG. 1A-1C show examplifying embodiments of medical devices with designed surfaces in accordance with the invention.
Figure 1B:
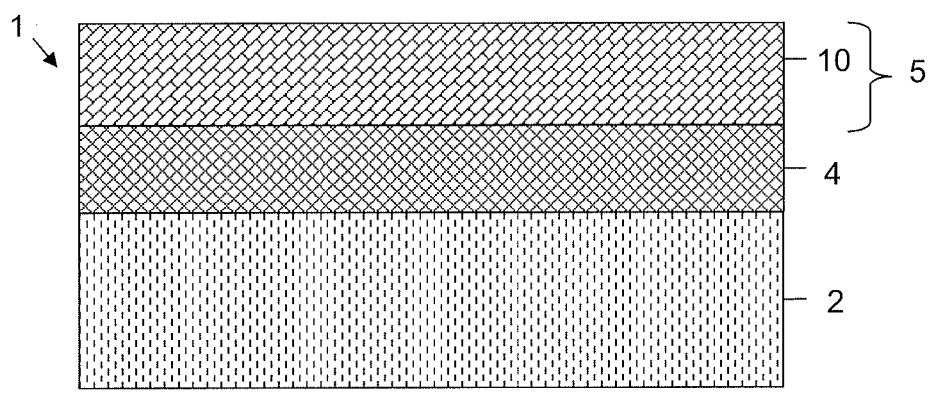

Two exemplifying embodiments of the invention are schematically shown in FIGS. 1A and 1B. FIG. 1A illustrates a medical device with a designed layered surface structure, the medical device comprising a metal substrate 2, a multilayered coating layer structure 5, comprising a first intermediate layer 6, a second intermediate layer 8 and a ceramic outermost layer 10, and a bonding structure 4 between the metal substrate 2 and the coating layer structure 5. FIG. 1B illustrates a medical device with an alternatively designed surface, the medical device comprising a metal substrate 2, a single layered coating layer structure 5 being a ceramic outermost layer 10, and a bonding structure 4 between the metal substrate 2 and the coating layer structure 5.

In short, the metal substrate 2 is the base material of the medical implant or instrument, or of a part or component of the medical implant or instrument. It comprises a metal or metal alloy, preferably with chemical and mechanical properties that are suitable for medical implants or instruments, e.g. a cobalt chromium (CrCo) based alloy or stainless steel.

The bonding structure 4 is deposited atop the substrate before the subsequent addition of the optional intermediate layer or layers and/or the outermost layer 10. It provides a smooth transition of mechanical and/or structural properties between the metal substrate 2 and the layer or layers that are closer to the surface. The bonding structure 4 has a hardness which lies between the hardness of the metal substrate 2 and the coating layer structure 5. It also has a structural resemblance to the metal substrate 2 and/or the most adjacent layer of the coating layer structure 5, thereby providing a structural matching between the layers and functioning as a glue.

Figure 1C:
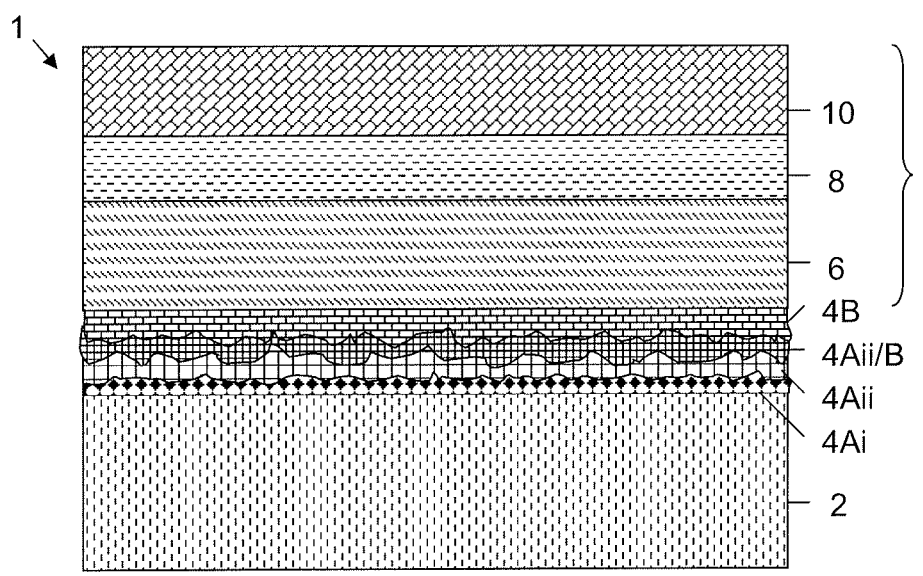

These properties are achieved according to a preferred embodiment of the invention by the design of the bonding structure 4, shown in FIG. 1C, which comprises a chromium rich layer 4A and a composition gradient 4Aii/4B with increasing proportions of a material having structural correspondence with the most adjacent layer of the coating layer structure. Atop the bonding structure any single or multiple layer structure having a suitable ceramic outermost layer 10 can be deposited.

The outermost layer 10 provides a surface with the necessary tribological and chemical properties that are needed for the medical implant or instrument, i.e. in terms of hardness, wear resistance, corrosion resistance and biocompatibility. In particular it provides a very hard and wear resistant surface. In different exemplifying embodiments, the outermost layer comprises aluminum oxide ($Al_2O_3$), zirconium oxide ($ZrO_2$), zirconium carbonitride (ZrCN), titanium boron nitride (TiBN), titanium carbonitride (TiCN) or combinations thereof.

The optional intermediate layer or layers 6, 8 in the embodiment shown in FIGS. 1A and 1C, are devised to provide for a smooth transition in hardness or other mechanical or chemical properties between the metal substrate 2 or bonding structure 4 and the outermost layer 10. The intermediate layer(s) may, e.g. comprise intermetallic nitrides or intermetallic carbonitrides, such as titanium carbonitride (TiCN) or zirconium carbonitride (ZrCN) or combinations thereof.

The designed layered surface structure of the medical device of the present invention may fully or partly cover the surface of the medical device. Typically the designed layered structure is devised on surfaces that are exposed to high loads and much abrasive wear, e.g. bearing surfaces that are configured to articulate or move against other surfaces, or surfaces that have to be resistant to corrosion.

Process for Providing a Bonding Structure in a Designed Layer Structure

The designed layered surface structure is accomplished by a process according to the present invention, one embodiment shown schematically in FIG. 2A-G. The process comprises applying a layered structure to a metal substrate by a suitable method, including chemical vapor deposition (CVD), physical vapor deposition (PVD) and/or thermal spraying deposition. Preferably the respective layers are deposited by CVD, also referred to as "gas plating" or "vapor plating". The process results in a designed surface structure with a total thickness of about maximum 20 μm, e.g. 5-10 μm. The different layers comprise compounds directly derived from the deposition process and its chemical reactions, as well as transition layers there between, resulting from more indirect reactions and diffusion during the process. The different layers and transition layers provide a high degree of compatibility and adhesion between the substrate and the respective layers, resulting in a surface that is able to withstand separation even under heavy loads and repeated articulation in relation to the outermost layer.

The term "metal substrate" refers to the material or the structure by which a substantial part or the core of the medical implant or instrument is made or shaped of. It may constitute the entire or nearly entire medical device, or may be a part or component of the medical device, where the remainder of the medical device comprises some other material. The metal substrate 2 comprises a metal or metal alloy, preferably with chemical and mechanical properties that are suitable for medical implants or instruments. For example, it should be ductile, in order to lessen the risk of fracture due to brittleness, and/or corrosion resistant. In addition it is preferably biocompatible (i.e. is not toxic or allergenic) and has appropriate strength and fatigue characteristics. The substrate 2 should also preferably and as in most embodiments comprise at least traces of carbon. Exemplary metal substrates 2 include cobalt based alloys, stainless steel, titanium or titanium based alloys, zirconium or zirconium based alloys. In a preferred embodiment of the present invention the metal substrate 2 comprises stainless steel or a cobalt (Co) based metal alloy such as a cobalt chromium (CoCr) based alloy or a cobalt chromium molybdenum (CoCrMo) based alloy. Suitable alloys include cast, forged and wrought cobalt-28-chromium-6-molybdenum (Co28Cr6Mo) alloys such as ASTM F75-01, ASTM F799-02 and ASTM F1537-00.

The bonding structure 4 is adhered to the part or parts of the metal substrate surface where the designed layer structure is desired. It provides a smooth transition of mechanical and/or structural properties between the metal substrate 2 and the coating layer structure 5. The hardness of the bonding structure 4 increases going from the region closest to the metal substrate 2 towards the region closest to the coating layer structure 5. The bonding structure comprises a layer deposited atop the metal substrate which is rich in chromium (Cr) or chromium based compounds such as chromium carbide (CrC) or chromium carbonitride (CrCN). In embodiments the chromium rich region 4A forms a single chromium rich layer, or alternatively and preferably a series 4Ai, 4Aii of thin layers of chromium compounds such as chromium carbide (CrC) and chromium carbonitride (CrCN).

The bonding structure 4 is also devised with a gradient layer 4Aii/4B having a composition gradient comprising, going from the substrate towards the surface, decreasing proportions of the chromium rich substances and increasing proportions of a gradient material 4B having structural correspondence with the next coming, most adjacent layer, of the coating layer structure. Such a material may, e.g. be intermetallic carbides, nitrides or carbonitrides such as titanium carbonitride (TiCN) or zirconium carbonitride (ZrCN).

The bonding structure is devised such that it has a structural correspondence with the metal substrate 2 and/or the most adjacent layer of the coating layer structure 5. The bonding structure thereby provides a structural matching between the layers which increases adhesion between the layers. For example, carbon diffuses from the substrate to the bonding structure and thereby generates a carbon comprising structure that is integrated with the substrate. The carbon diffusion also results in that the hardness is gradually increasing from the substrate and outwards through the bonding layer. In addition, the respective materials in the bonding structure and at least the most adjacent layer of the coating layer structure are structurally similar.

In this context it is meant by structural correspondence or similarity that the materials e.g. have similar cell axis parameters, i.e. that they have similar atom positions in the unit cells of crystal structures, although the size of the unit cells may vary according to atom size. The materials may further be chemically similar or compatible, i.e. have similar atomic structure and atomic properties, such that atoms in one of the materials may be exchanged with atoms from the other material, without altering the structure or cell parameters and still substantially keeping the chemical and mechanical properties of the material. Through these features the materials will not phase separate, but rather form a solid solution. Additionally or as a consequence of the structural correspondence or similarity the respective materials usually have similar physical and mechanical properties, i.e. they exhibit e.g. similar hardness, elastic modulus and/or thermal expansion coefficient.

Figure 2A:
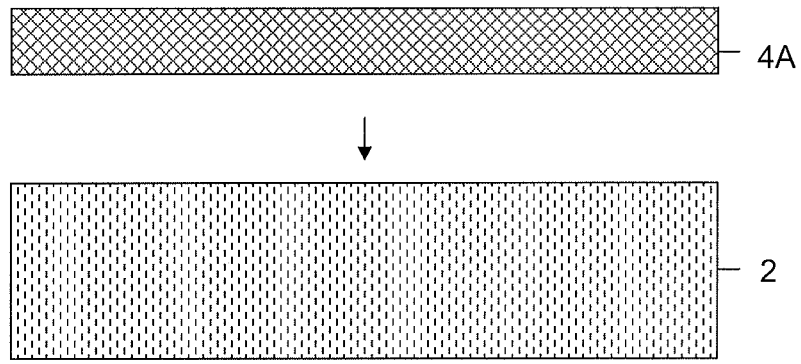
FIG. 2A-2H show an examplifying embodiment of a method for providing medical devices with designed surfaces in accordance with the invention.

The bonding structure 4 is produced by a process which is schematically illustrated in FIG. 2A-2F. The chromium rich layer 4A of the bonding structure 4 is deposited atop the surface of the metal substrate using, e.g. chemical vapor deposition (CVD) (FIG. 2A). As an example, a gas mixture of a chromium halide, such as chromium chloride ($CrCl_3$), and hydrogen ($H_2$), is passed into a chamber in which the metal substrate is located. The temperature may range from 800° C. to 1100° C. and should be below the melting point of the binder metal of the substrate. The chemical reaction in this example is: $2CrCl_3 + 3H_2 \rightarrow 2Cr + 6HCl$. The chromium will be deposited atop the metal substrate while the hydrochloric acid (HCl) is pumped out of the chamber. This is in one embodiment followed by a heat treatment in a temperature of, e.g. in the order of 900° C. during a period preferably in the order of 24 hours.

Figure 2B:
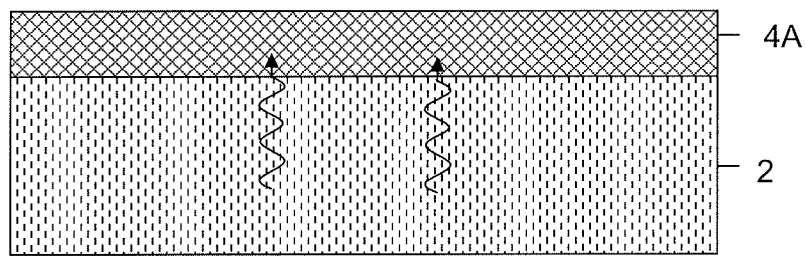
Figure 2C:
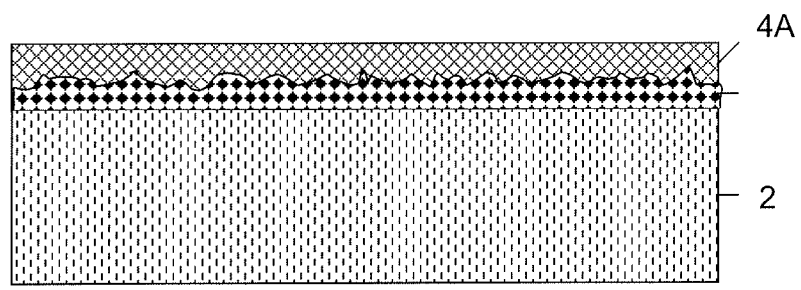

Should the metal substrate comprise traces of carbon a thin layer (0.1-2 μm), a first compound chromium layer 4Ai, of chromium carbide (CrC) will in most embodiments and preferably be formed closest to the substrate, through diffusion of carbon from the metal substrate into the chromium rich layer (FIGS. 2B and 2C).

Figure 2D:
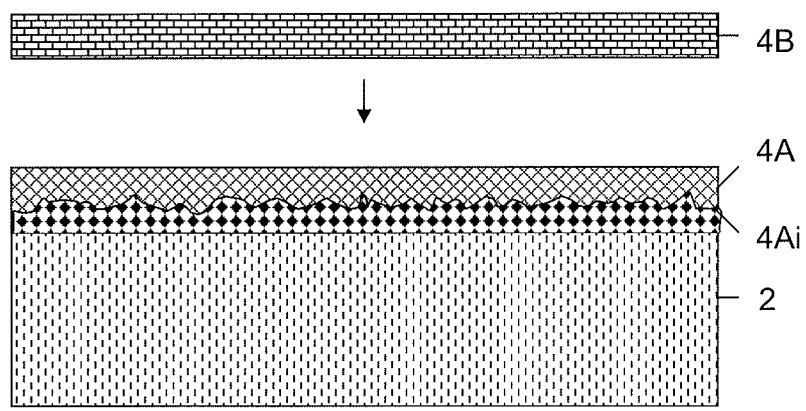

On top of the chromium rich layer 4A is deposited a gradient material 4B which structurally resembles the next coming, most adjacent layer, of the coating layer structure (FIG. 2D). As an exemplifying alternative, titanium carbonitride (TiCN) is deposited atop the chromium rich layer of the bonding structure, preferably by chemical vapor deposition (CVD). A gas mixture of a titanium halide, such as titanium chloride ($TiCl_4$), and gases comprising carbon and nitrogen, may be passed into a chamber in which the medical device is located. The temperature may range from about 800° C. to about 900° C. and is in a preferred embodiment 850° C.

Figure 2E:
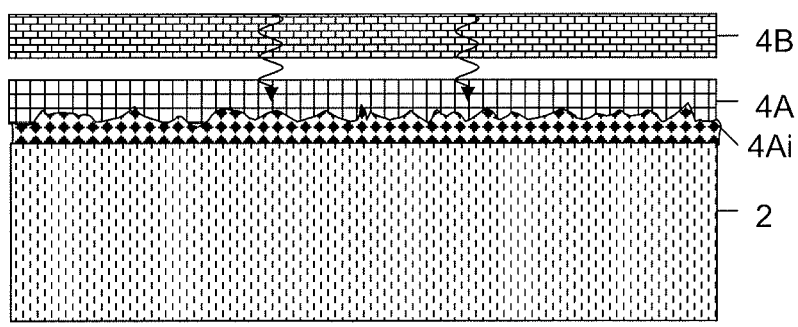
Figure 2F:
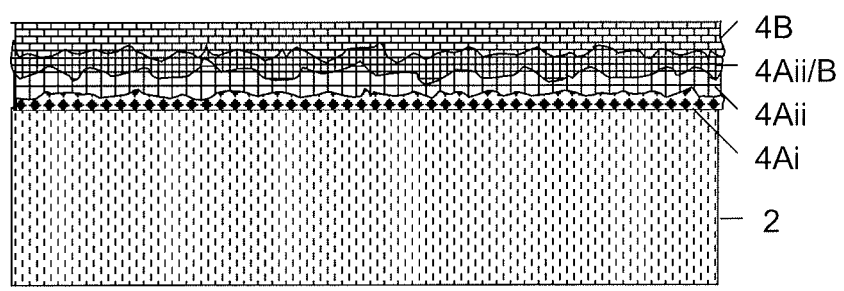

The carbon and nitrogen comprising gases will in this stage initially react with the chromium of the bonding structure, thereby creating a layer, a second chromium compound layer 4Aii, of chromium carbonitride (CrCN) on the surface (FIG. 2E). Thereby the chromium rich region forms a series of two chromium compound layers comprising CrC 4Ai and CrCN 4Aii respectively. As the process proceeds the titanium chloride ($TiCl_4$) will start reacting with the carbon and nitrogen. Titanium carbonitride (TiCN) 4B will initially be deposited along with the chromium carbonitride (CrCN) 4Aii, creating a region, herein called a gradient layer 4Aii/B where the two substances are intermingled (FIG. 2F). The process is in one embodiment continued until only or substantially only titanium carbonitride (TiCN) forms, thereby creating an outermost region of the bonding structure comprising only or substantially only titanium carbonitride 4B. In another embodiment the process is stopped earlier, yielding varying degrees of titanium carbonitride (TiCN) in the outermost region of the bonding structure. Since the intermetallic carbonitrides have corresponding structural and mechanical properties the transition from CrCN to TiCN, with a composition gradient comprising a mixture of the two substances, there will be tight adhesion in this transition.

As a result the bonding structure 4 will thus, in the exemplified embodiment, form a composition gradient comprising, starting from the region closest to the metal substrate and going outwards; a chromium rich region 4A, possibly in the form of chromium carbide (CrC) 4Ai and chromium carbonitride (CrCN) 4Aii, a gradient layer 4Aii/B comprising intermixed chromium carbonitride (CrCN) and titanium carbonitride (TiCN), and a titanium carbonitride (TiCN) region 4B.

The chromium rich bonding structure 4 described in the exemplified embodiment of the present invention thus provides an improved transition gradient of chemical, material and mechanical properties between the substrate 2 and the outer layers. The bonding structure 4 preferably has a thickness of about 1-5 μm. The chromium rich, or chromium carbide (CrC), layer 4Ai serves as a bridge between the underlying carbon comprising substrate 2 and the chromium carbonitride (CrCN) 4Aii above. The structure of the chromium carbonitride (CrCN) in its turn resembles the structure of the intermediate titanium carbonitride (TiCN) layer 4B above, thereby serving as a bridge or glue between the chromium rich, or chromium carbide (CrC), layer and the titanium carbonitride (TiCN) layer. This transition gradient in chemical, structural and mechanical properties improves the adhesion between the respective layers and thereby contributes to making the designed multilayered surface more resistant to cracking, peeling and wear.

Figure 2G:
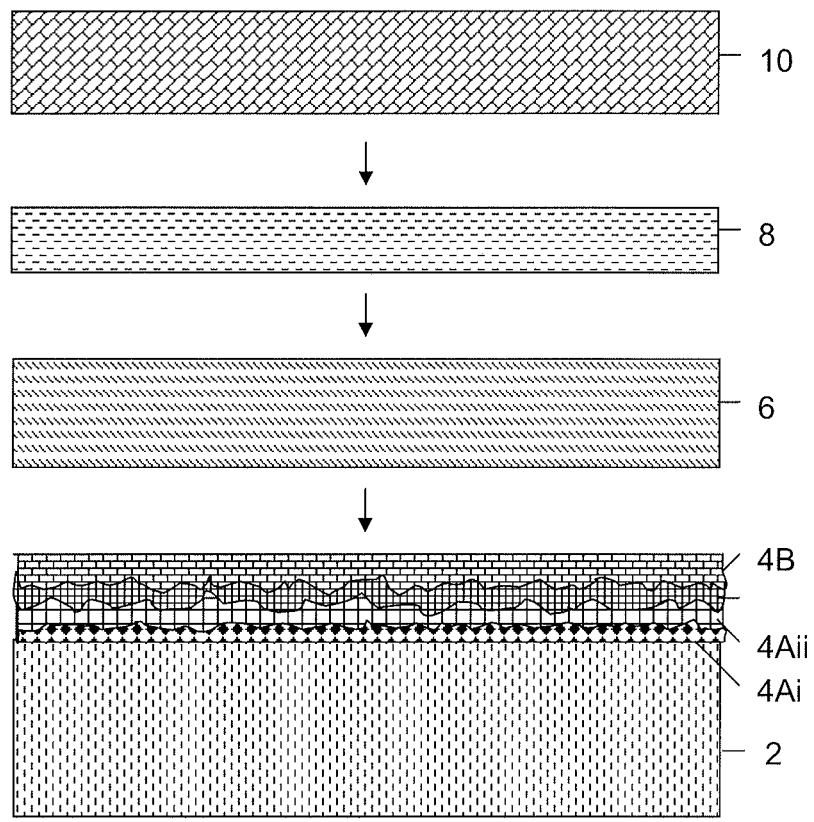
Figure 2H:
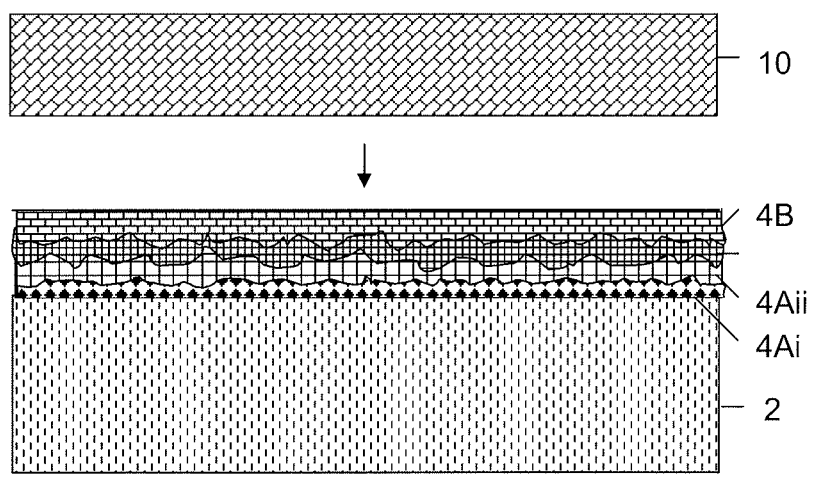

The metallic substrate 2 with the bonding structure 4 will now serve as a basis on top of which a coating layer structure 5 comprising a ceramic outermost layer 10 may be deposited. For example a coating layer structure 5 comprising several layers, including a ceramic outermost layer 10, may be deposited atop the bonding structure 4, as schematically illustrated in FIG. 2G. Alternatively a ceramic outermost layer 10 may be directly deposited atop the bonding structure 4, as schematically illustrated in FIG. 2H.

The layer which is most adjacent to the bonding structure 4 should comprise a material having structural correspondence with the material of the outermost region of the bonding structure 4.

Examples of Layered Coating Layer Structures

The coating layer structure 5 may comprise one or more intermediate layers 6, 8 the purpose of which is to further provide a smooth transition and good adherence between the metal substrate and the outermost layer. The intermediate layer(s) 6, 8 should thus preferably comprise a material which has one or more mechanical, chemical or physical properties (e.g. hardness, crystal structure, elastic modulus and/or chemical compatibility) that are intermediate between the corresponding properties of the metal substrate 2 and the outermost layer 10 and/or between the corresponding properties of the bonding structure 4 and the outermost layer 10. It will thereby, in addition to the bonding structure 4, further provide a transition gradient of those properties, and thereby also provide an increased level of adhesion between the metal substrate 2 and the outermost layer 10.

Examples of intermediate layers and coating layer structures have been described e.g. in the patent document US20070078521 A1 to DePuy. In embodiments where an intermediate layer 6 is arranged in direct contact with the bonding structure 4, the intermediate layer 6 comprises a material which has structural correspondence with the bonding structure 4. The intermediate layer 6, 8 may be applied to the bonding structure 4 by any suitable method, e.g. chemical vapor deposition (CVD), physical vapor deposition (PVD) or thermal spraying deposition (e.g. plasma spraying), to any suitable thickness that corresponds to the desired mechanical, chemical or physical properties. The thickness of the intermediate layer may vary between 0.001-10 μm, and is preferably in the range of 0.4-1 μm.

As an example, in an application of the present invention, a coating layer structure having an intermediate layer 6 comprising titanium carbonitride (TiCN) may e.g. be applied directly to the bonding structure 4. In continuation of the above exemplified embodiment, the titanium carbonitride (TiCN) of the intermediate layer 6 may be applied as a continuum of the above described CVD process, possibly by altering the temperature or other process parameters, to form a thicker layer of titanium carbonitride (TiCN), e.g. a layer with a thickness of about 0.4-1 μm.

An outermost layer 10 is applied over the intermediate layer(s) (FIG. 21). The purpose of the outermost layer 10 is to provide a surface which is strong and wear resistant and in addition is biocompatible, chemically inert and corrosion resistant. The outermost layer 10 comprises a ceramic material, as exemplified above, with a suitable thickness to provide the mentioned desired mechanical and chemical properties. The thickness may vary between 0.001-10 μm and in general it is preferably in the range of 0.5-10 μm. The outermost layer 10 may be applied to the intermediate layer, or directly onto the bonding structure, by any suitable method, e.g. chemical vapor deposition (CVD), physical vapor deposition (PVD) or thermal spraying deposition (e.g. plasma spraying)

The outermost layer 10 may e.g. comprise aluminum oxide ($Al_2O_3$), also referred to as alumina), of alpha or kappa phase (α- or κ-phase), preferably of α-phase. It may preferably be applied atop an intermediate layer of e.g. titanium carbonitride (TiCN), therby forming a multilayered coating layer structure. Aluminum oxide ($Al_2O_3$) may be deposited atop the titanium carbonitride (TiCN) using e.g. CVD or PVD or similar per se known coating techniques. In a preferred embodiment the aluminum oxide ($Al_2O_3$) is deposited by CVD. The thickness of the aluminum oxide ($Al_2O_3$) outermost layer is preferably in the range of 0.5-10 μm. The hardness of an aluminum oxide ($Al_2O_3$) outermost layer is approximately in the order of 30 GPa.

In an alternative application of the present invention an outermost layer 10 is deposited directly on top of the bonding structure 4. For example zirconium oxide (ZrO2) may be deposited directly onto a bonding structure comprising zirconium carbonitride (ZrCN) as a gradient material 4B, using e.g. CVD or PVD or similar per se known coating techniques, preferably by CVD. The thickness of the zirconium oxide (ZrO2) outermost layer is preferably in the range of 0.5-10 μm, yielding a hardness of approximately 15 GPa.

The outermost layer may optionally be further surface treated by, e.g. blasting, polishing, brushing or chemical-mechanical polishing.

The invention may, as has been described, be applied to medical instruments or components thereof. In a preferred embodiment the metal substrate 2 of such a medical instrument comprises stainless steel. In particular such a medical instrument or component thereof comprises a metal substrate 2 of stainless steel, with a coating layer structure 5 provided on its surface, where the coating layer structure 5 comprises at least an outermost layer 10 of a ceramic material. A bonding structure 4 is deposited between the metal substrate 2 and the coating layer structure 5. It comprises a chromium rich layer 4A which is deposited onto the metal substrate 2 surface and has a higher concentration of chromium than the metal substrate. The bonding structure 4 also comprises a gradient layer 4Aii/4B having a composition gradient from the chromium rich layer 4A towards the surface of the device providing increasing proportions of a gradient material 4B having structural correspondence with the layer of the coating layer structure 5 that is most adjacent to the bonding structure 4.

The invention claimed is:

1. A medical implant device or component thereof comprising:
   a) a metal substrate having a surface;
   b) a coating layer structure provided on the substrate and having an outermost layer of a ceramic material; and
   c) a bonding structure deposited between the metal substrate and the coating layer structure, said bonding structure comprising a chromium rich layer deposited onto the metal substrate surface and having a higher concentration of chromium than the metal substrate, and said bonding structure comprising a gradient layer having a composition gradient from the chromium rich layer towards the surface of the device providing increasing proportions of a gradient material having structural correspondence with the layer of the coating layer structure that is most adjacent to the bonding structure,
   wherein structural correspondence means that materials have similar cell axis parameters with similar atom positions in the unit cells of crystal structures, although the size of the unit cells may vary according to atom size.

2. The medical implant device of claim 1, wherein the gradient material of the bonding structure further having structural correspondence with the chromium rich layer.

3. The medical implant device of claim 1, wherein the metal substrate comprises an alloy comprising carbon.

4. The medical implant device of claim 1, wherein the chromium rich layer of the bonding structure comprises chromium carbide, CrC, chromium carbonitride, CrCN, and/or chromium nitride, CrN.

5. The medical implant device of claim 1, wherein the chromium rich layer of the bonding structure comprises a first chromium compound layer of chromium carbide, CrC, and a second chromium compound layer of chromium carbonitride, CrCN.

6. The medical implant device of claim 1, wherein the gradient material of the bonding structure comprises a selection of intermetallic carbides, intermetallic nitrides or intermetallic carbonitrides.

7. The medical implant device of claim 1, wherein the thickness of the bonding structure is in the range of 1-5 μm.

8. The medical implant device of claim 1, wherein the metal substrate comprises a cobalt based alloy or stainless steel.

9. The medical implant device of claim 1, wherein the outermost layer comprises a ceramic material selected from the group of aluminum oxide, $Al_2O_3$, zirconium oxide, $ZrO_2$, titanium carbonitride, TiCN, zirconium carbonitride, ZrCN or titanium boronitride, TiBN, or a combination thereof.

10. The medical implant device of claim 9, wherein the outermost layer comprises α- or κ-phase aluminum oxide, $Al_2O_3$.

11. The medical implant device of claim 9, wherein the thickness of the outermost layer is in the range of 0.5 to 10 μm.

12. The medical implant device of claim 1, wherein the coating layer structure further comprises an intermediate layer between the bonding structure and the outermost layer, the intermediate layer being in direct contact with the bonding structure.

13. The medical implant device of claim 12, wherein the thickness of the intermediate layer is in the range of 0.1-10 μm.

14. The medical implant of claim 1, wherein the intermediate layer comprises a material selected from the group comprising of intermetallic nitrides or intermetallic carbonitrides or combinations thereof.

15. A medical implant device or component thereof comprising:
   a) a metal substrate comprising cobalt based alloy or stainless steel, having a carbon content and having a surface;
   b) a coating layer structure provided on the substrate, having an intermediate layer comprising titanium carbonitride, TiCN, and having an outermost layer comprising aluminum oxide, $Al_2O_3$; and
   c) a bonding structure deposited between the metal substrate and the coating layer structure, said bonding structure comprising a chromium rich layer deposited onto the metal substrate surface and having a higher concentration of chromium than the metal substrate, and said bonding structure comprising a gradient layer having a composition gradient from the chromium rich layer towards the surface of the device providing increasing proportions of titanium carbonitride, TiCN,
   wherein the bonding structure has structural correspondence with the coating layer structure, and
   wherein structural correspondence means that materials of the bonding structure and materials of the coating layer structure have similar cell axis parameters with similar atom positions in the unit cells of crystal structures, although the size of the unit cells may vary according to atom size.

16. The medical implant device of claim 15, wherein the chromium rich layer comprises a first chromium compound layer of chromium carbide, CrC, and a second chromium compound layer of chromium carbonitride, CrCN.

17. A method of providing a medical implant device or component thereof, the method comprising:
   a) providing a medical implant device or component thereof comprising a metal substrate having a surface;
   b) depositing, in a temperature in the range of 800° C.-1100° C., chromium onto at least a portion of the metal substrate surface, thereby creating a chromium rich layer on the metal substrate surface;
   c) depositing onto the chromium rich layer a gradient layer of a material composition such that increasing proportions of a gradient material appear outwardly from the chromium rich layer;
   d) depositing onto the gradient layer a material forming a first layer of a coating layer structure adjacent to the gradient layer, said first layer of the coatings structure having structural correspondence with the gradient material,
   wherein structural correspondence means that materials of the first layer of the coating structure and of the gradient material have similar cell axis parameters with similar atom positions in the unit cells of crystal structures, although the size of the unit cells may vary according to atom size.

18. The method of claim 17, wherein the gradient layer is deposited such that the surface of the chromium rich layer forms a material having a structural correspondence with the gradient material.

19. The method of claim 18, wherein the gradient material comprises a selection of intermetallic carbides, intermetallic nitrides or intermetallic carbonitrides.

20. The method of claim 18, wherein the metal substrate comprises a cobalt based alloy, or stainless steel.

21. A medical implant device provided by the method of claim 18.

22. The method of claim 17, wherein the metal substrate comprises an alloy having a carbon content.

23. The method of claim 17, wherein the chromium rich layer forms chromium carbide, CrC, chromium carbonitride, CrCN, and/or chromium nitride, CrN.

24. The method of claim 23, wherein the chromium rich layer forms a first chromium compound layer of chromium carbide, CrC, and a second chromium compound layer of chromium carbonitride, CrCN.

* * * * *